(12) United States Patent
Rattan et al.

(10) Patent No.: US 12,649,920 B2
(45) Date of Patent: Jun. 9, 2026

(54) USE OF DNA:RNA DUPLEX FRAGMENTATION

(71) Applicant: Bio-Rad Laboratories, Inc., Hercules, CA (US)

(72) Inventors: Rahul Rattan, Brighton, MI (US); Jeffrey Perry, Plymouth, MI (US); Marta Gonzalez-Plasky, Grosse Pointe Woods, MI (US); Stephanie Spohn, Ypsilanti, MI (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 728 days.

(21) Appl. No.: 18/073,377

(22) Filed: Dec. 1, 2022

(65) Prior Publication Data

US 2023/0174973 A1 Jun. 8, 2023

Related U.S. Application Data

(60) Provisional application No. 63/285,402, filed on Dec. 2, 2021.

(51) Int. Cl.
| | |
|---|---|
| *C12Q 1/68* | (2018.01) |
| *C12N 15/10* | (2006.01) |
| *C12Q 1/6855* | (2018.01) |
| *C12Q 1/6874* | (2018.01) |

(52) U.S. Cl.
CPC ....... *C12N 15/1096* (2013.01); *C12Q 1/6855* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 6,297,017 B1 | 10/2001 | Schmidt et al. | |
| 2011/0281736 A1 | 11/2011 | Drmanac et al. | |
| 2015/0284789 A1* | 10/2015 | Hogers | ............... C12Q 1/6874 |
| | | | 435/6.12 |
| 2015/0337295 A1 | 11/2015 | West et al. | |
| 2016/0046975 A1 | 2/2016 | Rashtchian et al. | |
| 2018/0002751 A1* | 1/2018 | Van Eijk | .............. C12Q 1/6869 |
| 2021/0190770 A1 | 6/2021 | Delaney et al. | |
| 2021/0207109 A1 | 7/2021 | Bibillo et al. | |

FOREIGN PATENT DOCUMENTS

| | | | |
|---|---|---|---|
| WO | 2004/024953 A1 | 3/2004 | |
| WO | WO-2018196763 A1 * | 11/2018 | ........... C12Q 1/6806 |

OTHER PUBLICATIONS

International Search Report and Written Opinion in PCT/US2022/051574 mailed Jul. 28, 2023; 14 pages.
Bai, M. et al.; Ca$^{2+}$-dependent nuclease is involved in DNA degradation during the formation of the secretory cavity by programmed cell death in fruit of *Citrus grandis* 'Tomentosa'; *Journal of Experimental Botany;* vol. 71, No. 16; Apr. 23, 2020; pp. 4812-4827.

(Continued)

*Primary Examiner* — Aaron A Priest
(74) *Attorney, Agent, or Firm* — Kilpatrick Townsend and Stockton LLP

(57) ABSTRACT

Methods of generating cDNAs from RNA involving cleavage of DNA/RNA complexes are provided.

14 Claims, 5 Drawing Sheets

Specification includes a Sequence Listing.

(56) References Cited

OTHER PUBLICATIONS

New England Biolabs Inc.; "Quick Tips—Do I need a 5' phosphate for ligation?"; Sep. 29, 2020; retrieved from the internet on May 11, 2023 at https://web.archive.org/web/20200929020229/https://www.neb.com/tools-and-resources/video-library/do-i-need-a-5-phosphate-for-ligation; 3 pages.

Kisiala, M. et al.; "Restriction endonucleases that cleave RNA/DNA heteroduplexes bind dsDNA in A-like conformation"; *Nucleic Acids Research;* vol. 48, No. 12; Jul. 9, 2020; pp. 6954-6969.

Murray I.A. et al.; "Sequence-specific cleavage of RNA by Type II restriction enzymes"; *Nucleic Acids Research*; vol. 38, No. 22; Dec. 2010; pp. 8257-8268.

Ziegenhain, C. et al.; "Comparative Analysis of Single-Cell RNA Sequencing Methods"; *Molecular Cell*; vol. 65, No. 4; Feb. 16, 2017; pp. 631-643.

Ohtsubo, Y. et al.; "Optimization of single strand DNA incorporation reaction by Moloney murine leukaemia virus reverse transcriptase"; *DNA* Research; vol. 25, Issue 5, Oct. 2018, pp. 477-487.

Wulf, M.G. et al.; "Non-templated addition and template switching by MMLV-based reverse transcriptases co-occur and compete with each other"; *J Biol Chem*; vol. 294, No. 48; Nov. 29, 2019; pp. 18220-18231.

Zajac, P. et al.; "Base Preferences in Non-Templated Nucleotide Incorporation by MMLV-Derived Reverse Transcriptases"; *PLoS ONE*; vol. 8, Issue 1; Dec. 2013; e85270; 13 pages.

Nilsen, I.W. et al.; "The Enzym and the cDNA Sequence of a Thermolabile and Double-Strand Specific DNase from Northern Shrimps (*Pandalus borealis*)"; *PLoS ONE*; vol. 5, Issue 4; Apr. 2010; e10295; 9 pages.

Extended European Search Report in EP22902196 mailed Oct. 13, 2025; 7 pages.

* cited by examiner

USE OF DNA:RNA DUPLEX FRAGMENTATION

CROSS-REFERENCE TO RELATED PATENT APPLICATIONS

The present patent application claims benefit of priority to U.S. Provisional Patent Application No. 63/285,402, filed Dec. 2, 2021, which is incorporated by reference for all purposes.

SEQUENCE LISTING

The instant application contains a Sequence Listing which has been submitted electronically in XML format and is hereby incorporated by reference in its entirety. Said XML copy, created on Feb. 21, 2023, is named 094868_1358219_118810US_SL.xml and is 11,219 bytes in size.

BACKGROUND OF THE INVENTION

Efficient capture of RNA, conversion into cDNA, and production of sequencing libraries is required for sensitivity with single cell applications. The assay input of a single cell has relatively few transcripts available for capture, so a loss of efficiency in any one of these steps results in loss of gene coverage and diversity, for example, several low transcript genes are thought to have as few as 5-12 copies per cell.

Some methods for producing a sequencing library have been described previously. One approach is to use Moloney murine leukemia virus (MMLV)-type reverse transcriptases with their terminal transferase and template switch activities. The enzyme's terminal transferase abilities involve the tendency to insert several deoxycytosines (+CCC) at the 3'-end of newly synthesized cDNAs. The enzyme can then switch templates if a new sequence containing complementary guanosine nucleotides (rGrGrG) hybridizes to the 3'-end of cDNAs. These sequences are often referred to as a template switch oligonucleotides and can be used to add adapters, such as those required for sequencing into cDNA molecules to tag them. However, the reverse transcriptase enzyme may also incorporate other nucleotides at the 3'-end of cDNAs and, at best, only 46% of cDNA sequences would be complementary to most common template switch oligonucleotides. The inefficiencies are compounded if the enzyme is unable to complete the template switch as this process, by itself, can be very inefficient with only about 10-40% of cDNA molecules incorporating adapter tags. The end result is the loss of low abundance gene transcripts as well as overall transcripts' diversity.

Another approach is to amplify the complement strand of the newly synthesized cDNA molecule using degenerate primers with a 5' tag sequence, referred to as second strand synthesis. After second strand synthesis, the cDNA can be converted into a sequenceable library using a standard sequencing library kit incorporating TA ligation approaches, or through bead size-selection approaches with downstream indexing PCR. The second strand synthesis approach can also be inefficient and biased due to the potential of degenerate primers selecting for GC-rich and short cDNA transcripts. In addition, the requirement of a sequencing library kit with fragmentation adds an inefficient library preparation convoluted to an enrichment approach to obtain fragments with single cell barcode sequences.

BRIEF SUMMARY OF THE INVENTION

In some embodiments, the disclosure provides methods of generating a cDNA from RNA. In some embodiments, the methods comprise generating a first strand cDNA from the RNA by contacting the RNA with one or more primer that anneals to the RNA and extending the primer with a reverse transcriptase, thereby forming a DNA/RNA complex; cleaving the DNA/RNA complex with at least one restriction enzyme or endonuclease that cleaves the DNA/RNA complex and leaves a 3' DNA end and a 5' RNA end; ligating a 5' phosphorylated oligonucleotide to the 3' DNA end to form a first strand cDNA comprising 5'-3': the primer, first strand cDNA and the oligonucleotide; and amplifying the first strand cDNA.

In some embodiments, the RNA is mRNA.

In some embodiments, the ligating comprises annealing a double-stranded oligonucleotide comprising a 5' phosphorylated end to a sequence at the 3' DNA end and contacting the annealed oligonucleotide with a ligase, thereby ligating the 5' phosphorylated end of the oligonucleotide to the 3' DNA end. In some embodiments, the sequence at the 3' DNA end of the cleaved DNA/RNA complex is a single-stranded overhang. In some embodiments, after the cleaving and before the ligating the DNA/RNA complex is disassociated. In some embodiments, the DNA/RNA complex is disassociated by heat.

In some embodiments, the 5' RNA end is a single-stranded overhang; and the ligating comprises annealing a 5' phosphorylated oligonucleotide to the 5' RNA overhang sequence and contacting the annealed oligonucleotide with a ligase, thereby ligating the oligonucleotide to the 3' DNA end.

In some embodiments, the generating, cleaving ligating and amplifying occur in a single reaction vessel.

In some embodiments, the primer comprises a poly dT 3' end that anneals to a 3' poly A sequence on the mRNA.

In some embodiments, the primer comprises a gene-specific 3' end that specifically anneals to specific mRNA.

In some embodiments, one or more primer comprises a plurality of primers having different gene-specific 3' ends that specifically anneal to different specific mRNA.

In some embodiments, after the cleaving and before the ligating end repair is performed on the cleaved DNA/RNA complex. In some embodiments, the end repair comprises contacting the cleaved DNA/RNA complex with alkaline phosphatase.

In some embodiments, the cleaving comprises cleaving the DNA/RNA complex with the at least one restriction enzyme. In some embodiments, the restriction enzyme is selected from the group consisting of AvaII, AvrII, BanI, BstNI, MvaI, HaeIII, HinfI, NciI, PFLMI, Sau3AI, and TaqI.

In some embodiments, the at least one restriction enzyme comprises two or more restriction enzymes that recognize different recognition sequences. In some embodiments, the two or more restriction enzymes are selected the group consisting of AvaII, AvrII, BanI, BstNI, MvaI, HaeIII, HinfI, NciI, PFLMI, Sau3AI, and TaqI.

In some embodiments, the cleaving comprises cleaving the DNA/RNA complex with the at least one endonuclease. In some embodiments, the at least one endonuclease is NUCL. In some embodiments, cleavage of the DNA/RNA complex with the endonuclease leaves a 3' DNA (i.e., cDNA) end and the RNA remains intact and is subsequently disassociated (e.g., by heat) or degraded. In some of these embodiments, the 5' phosphorylated oligonucleotide and a complementary oligonucleotide having a universal, degenerate or random 3' overhang end sequence is combined with the cDNA, the 3' overhang end sequence of the complementary oligonucleotide is annealed to the 3' end of the cDNA and the 5' phosphorylated oligonucleotide is ligated to the 3' end of the cDNA.

In some embodiments, the generating, cleaving, annealing and ligating is performed in a plurality of partitions. In some embodiments, the partitions are droplets or wells. In some embodiments, the partitions are permeabilized and fixed cells. In some embodiments, contents of the partitions are combined after the ligating and before the amplifying.

In some embodiments, the primer comprises a barcode and a first PCR handle sequence. In some embodiments, the barcode is a unique molecular identifier (UMI).

In some embodiments, the primer comprises a partition-specific barcode and a first PCR handle sequence. In some embodiments, the primer further comprises a unique molecular identifier (UMI).

In some embodiments, the oligonucleotide comprises 5'-3': a reverse complement of the 5' RNA overhang sequence and a second PCR handle or a fragment thereof or at least three contiguous nucleotides.

In some embodiments, the amplifying comprises polymerase chain reaction (PCR).

In some embodiments, the amplifying comprises isothermal amplification.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a bead" includes a plurality of such beads and reference to "the sequence" includes reference to one or more sequences known to those skilled in the art, and so forth.

An "oligonucleotide" is a polynucleotide. Generally oligonucleotides will have fewer than 250 nucleotides, in some embodiments, between 4-200, e.g., 10-150 nucleotides.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification. In an exemplary embodiment, amplifying refers to PCR amplification using a first and a second amplification primer.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

A "template" refers to a polynucleotide sequence that comprises the polynucleotide to be amplified, flanked by or a pair of primer hybridization sites. Thus, a "target template" comprises the target polynucleotide sequence adjacent to at least one hybridization site for a primer. In some cases, a "target template" comprises the target polynucleotide sequence flanked by a hybridization site for a "forward" primer and a "reverse" primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A "polymerase" refers to an enzyme that performs template-directed synthesis of polynucleotides, e.g., DNA and/or RNA. The term encompasses both the full-length polypeptide and a domain that has polymerase activity. DNA polymerases are well-known to those skilled in the art, including but not limited to DNA polymerases isolated or derived from *Pyrococcus furiosus, Thermococcus litoralis,* and *Thermotoga* maritime, or modified versions thereof. Additional examples of commercially available polymerase enzymes include, but are not limited to: Klenow fragment (New England Biolabs® Inc.), Taq DNA polymerase (QIA-GEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein a "barcode" is a short nucleotide sequence (e.g., at least about 4, 6, 8, 10, 12, 15, 20, 50 or 75 or 100 nucleotides long or more) that identifies a molecule to which it is conjugated or from the partition in which it originated. Barcodes can be used, e.g., to identify molecules originating in a partition, bead, or spot as later sequenced from a bulk reaction. Such a barcode can be unique for that partition, bead or spot as compared to barcodes present in other partitions, bead or spot. For example, partitions containing target RNA from single-cells can be subject to reverse transcription conditions using primers that contain different partition-specific barcode sequence in each partition, thus incorporating a copy of a unique "cellular barcode" (because different cells are in different partitions and each partition has unique partition-specific barcodes) into the reverse transcribed nucleic acids of each partition. Thus, nucleic acid from each cell can be distinguished from nucleic acid of other cells due to the unique "cellular barcode." In some embodiments described herein, barcodes described herein uniquely identify the molecule to which it is conjugated, i.e., the barcode acts as a unique molecular identifier (UMI). The length of the underlying barcode sequence determines how many unique samples can be differentiated. For example, a 1 nucleotide barcode can differentiate 4, or fewer depending on degeneracy, different partitions; a 4-nucleotide barcode can differentiate $4^4$ or 256 partitions or less; a 6-nucleotide barcode can differentiate 4096 different partitions or less; and an 8-nucleotide barcode can index 65,536 different partitions or less.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel or well. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

DETAILED DESCRIPTION OF THE INVENTION

Figure 1:
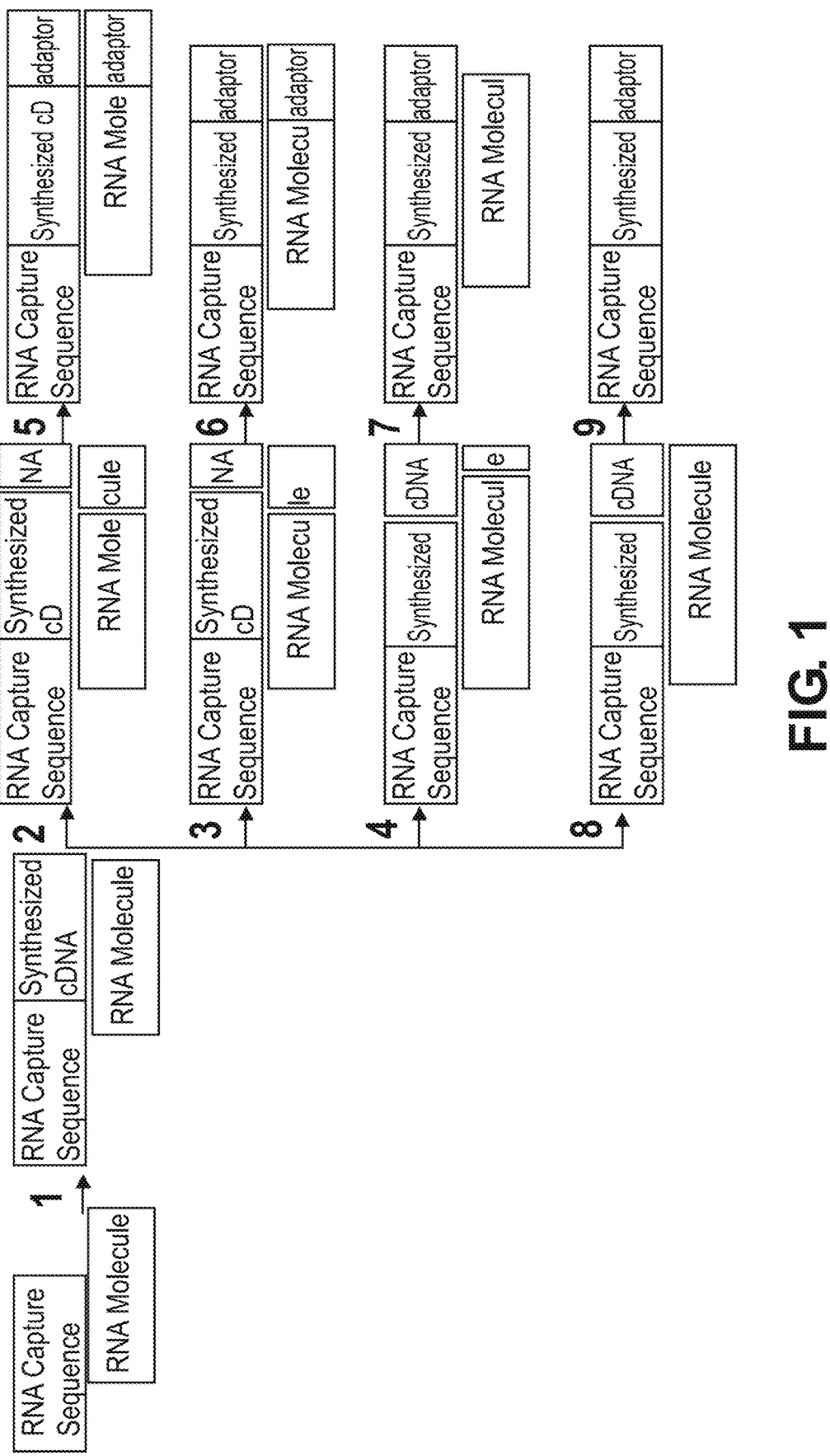
FIG. 1: Ligation Strategies after RNA:DNA heteroduplex digestion. RNA can be captured with a reverse transcription (RT) primer comprising at its 3' end, for example, a poly dT sequence or a gene specific sequence. In some embodiments, more than one RT primer is included such that a plurality of gene specific sequences are represented in the RT primers. Once annealed to the RT primer, cDNA is synthesized using reverse transcription (1). Next, one or more restriction enzymes are introduced to cleave the DNA:RNA heteroduplex, leaving a DNA overhang (2), or a blunt end (3), or an RNA overhang (4). Three general strategies can be implemented after digestion to add a DNA adaptor sequence to the 3' DNA end of the cleaved cDNA molecule. In some embodiments, a double-stranded DNA adaptor is annealed to the DNA overhang and a strand of the adaptor is ligated to the 3' DNA end of the cleaved DNA:RNA heteroduplex (5). In some embodiments, a blunt ligation can be performed by ligating a blunt ligation adaptor to the blunt RNA:DNA heteroduplex (6). Options 5 and 6 can be performed in the heteroduplex intact or the RNA can be disassociated from the DNA. Finally, in some embodiments, preserving the association of the RNA:DNA heteroduplex will allow ligation of a single stranded DNA adaptor sequence by complementing the RNA overhang left by the restriction enzyme (7). All three ligation approaches can be facilitated by for example, T4 DNA ligase, or approaches can be more selective using, for example, RNA dependent DNA ligase enzymes, or sticky end specific enzymes including but not limited to *E. coli*. DNA ligase.

A new way of generating cDNAs has been developed that allows for high efficiency in capturing cDNAs representative of an mRNA population, including rare low abundance mRNAs. As described herein, methods of generating cDNAs can involve forming a first strand cDNA using the mRNA or other RNA as a template, cleaving the resulting first strand cDNA/mRNA hybrid with a restriction enzyme that cleaves the RNA/DNA hybrids followed by ligation of an oligonucleotide to the 3' end of the first strand cDNA, thereby creating a first strand cDNA with PCR handles at both ends. Moreover, in embodiments involving digestion with DNA/RNA duplex-specific nucleases, the average size of fragments can be controlled (e.g., based on length of time of the digestion), allowing for selection preferred size ranges, e.g., for downstream applications such NGS that can use or require a smaller cDNA size for optimal sequencing.

The ligation can be highly efficient and thus allows for the generation of a first cDNA molecule with PCR handles at both 3' and 5' ends without, for example, template-switching or other methods for second strand synthesis. Having generated the first strand cDNA with PCR handles at both ends, PCR amplification can be readily used to prepare the template for nucleotide sequencing.

First strand cDNA synthesis can be performed as known in the art. Any RNA sample can be used. The term "RNA sample" refers to an RNA-containing sample. For example, an RNA sample can be a sample containing RNAs isolated from a starting material. An RNA sample can further contain DNAs isolated from the starting material. In some embodiments, an RNA sample contains RNA molecules that have been isolated from a starting material and further fragmented. In other cases, an RNA sample is derived from a directly lysed sample without specific nucleic acid isolation.

Reverse transcription (RT) is an amplification method that copies RNA into DNA. RT reactions can be performed with reaction mixtures as described herein. For example, the disclosure provides for reverse transcribing one or more RNA (including for example, all RNA in a cell, e.g., to make a cDNA library, or targeted RNA sequences) under conditions to allow for reverse transcription and generation of a first strand cDNA. The RT reaction can be primed with an RT primer that primes an RT reaction from at least one target RNA molecule. Exemplary RT primers can include, but are not limited to, those having a 3' end sequence that anneals to target RNA. For example the 3' end sequence can be one that is random, an oligo dT (also referred to herein as a "poly T") sequence, or an RNA-specific sequence. Oligo dT sequences are single stranded sequences of deoxythymine (dT). The length of the oligo dT sequence can vary, for example from 6 bases to 30 bases and may be a mixture of oligo dT sequences with different lengths. Components and conditions for RT reactions are generally known.

In addition to a 3' end sequence that anneals to the target RNA, the RT primer can also include one or more barcode sequence as well as a PCR handle sequence, i.e., a sequence that can be added to the end of all resulting cDNA sequences such that the entire set of different cDNAs can be amplified later with a universal primer. Exemplary PCR handle sequences can include but are not limited to universal sequences used in various sequencing platforms, including but not limited to the P5/P7 sequences from Illumina (e.g., P5 primer CGACGCTCTTCCGATCT (SEQ ID NO: 1) and P7 primer CGTGTGCTCTTCCGATCT (SEQ ID NO: 2)), PacificBio, or Ion Torrent. The barcode sequences can include, for example, a sample, partition-specific (e.g., bead-specific for embodiments in which individual beads carrying oligonucleotides are introduced into partitions) and/or sample barcode.

RT amplification reaction mixtures can be prepared as is known. In some embodiments, the amplification reaction mixture comprises one or more target-specific amplification primers. In some embodiments, the amplification mixture further comprises one or more of salts, nucleotides, buffers, stabilizers, reverse transcriptase, DNA polymerase, a detectable agent, and nuclease-free water. Exemplary methods of digital RT-PCR are described in, e.g., Sedlak et al., *J Clin Microbiol* 55:442-449 (2014).

Suitable reverse transcriptases can include but are not limited to Maxima RNAse+ (Thermo), Maxima RNAse− (Thermo), murine leukemia virus (MLV) reverse transcriptase (Gerard and Grandgenett, Journal of Virology 15:785-797, 1975; Verma, Journal of Virology 15:843-854, 1975), feline leukemia virus (FLV) reverse transcriptase (Rho and Gallo, Cancer Lett., 10:207-221, 1980, bovine leukemia virus (BLV) (Demirhan et al., Anticancer Res., 16:2501-5, 1996; Drescher et al., Arch Geschwulstforsch., 49:569-79, 1979), Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT III reverse transcriptase (U.S. Pat. Nos. 8,541,219, 7,056,716, 7,078,208), THERMOSCRIPT reverse transcriptase and MMLV RNase H-reverse transcriptase and Sensiscript (Qiagen).

The methods described herein comprise providing a first strand cDNA molecule annealed with its RNA template, referred to herein as a "cDNA/RNA complex" or "DNA/RNA complex," and cleaving the DNA/RNA complex with one or more DNA/RNA-cleaving restriction enzymes or endonucleases to generate DNA/RNA complex comprising the RT primer sequence, a portion of the extended RT primer (being complementary to a portion of the target RNA) and at least a portion of the complementary RNA, wherein the first strand cDNA has a new 3' end resulting from cleavage by the restriction enzyme.

Cleaving of the DNA/RNA complex can be achieved using one or more than one (e.g., 2, 3, 4, or more) different restriction enzymes or endonucleases. As any particular DNA/RNA complex may or may not have a particular restriction enzyme recognition sequence, in some embodiments, it can be advantageous to include more than one different restriction enzymes such that a higher proportion of DNA/RNA complexes are cleaved.

In some embodiments, depending on the restriction enzyme used, the resulting cleavage site in the DNA/RNA complex can result in an RNA single-stranded overhang sequence, a DNA single-stranded overhang sequence or a blunt end. Exemplary restriction enzymes that cleave DNA/RNA complexes and that can be used include but are not limited to AvaII, AvrII, BanI, BstNI, MvaI, HaeIII, HinfI, NciI, PFLMI, Sau3AI, or TaqI.

In other embodiments, an endonuclease that cleaves DNA/RNA duplexes is used. Such endonucleases for example cleave the DNA strand of RNA/DNA duplexes without cleaving the RNA strand or cleaving DNA/DNA duplexes or single-stranded nucleic acids. Such nucleases cleave within a duplex rather than at the end of the duplex (i.e., they ae not exonucleases) and are not sequence-specific, meaning that they cleave at sequences in a random manner. Exemplary endonucleases can include, but are not limited to, duplex-specific nuclease derived from the hepatopancreas of the Red King Crab, also called NUC1 or duplex-specific nuclease. See, e.g., Nilsen, et al., *PLoS ONE* 2010; 5(4): e10295. Cleavage by duplex specific nuclease leaves a 3' hydroxyl, allowing for appropriate ligation in subsequent steps as described herein.

In embodiments in which a non-specific endonuclease that cleaves DNA/RNA duplexes is used, in some aspects the endonuclease is used at a temperature below its optimal temperature, for example in some embodiments, the endonuclease is used at a temperature of 40-60° or 45-65°, or 45-55°, e.g., around 50° C. In some embodiments, the temperature is selected such that the RNA/DNA duplex is maintain (the temperature is not so high that the duplex is disassociated) and thus be cleaved by the endonuclease.

One advantage of using an endonuclease as described herein is that a portion of the RNA capture oligonucleotide sequence can be single-stranded (see, e.g., FIG. 4) and in view of the specificity of the endonucleases described herein for RNA/DNA duplexes (not cleaving single-stranded sequences), sequences in the single-stranded portion will not be cleaved by the endonuclease. Thus, barcodes or other sequences in the single-stranded portion will remain intact and will not be degraded prior to sequencing.

Optionally, after restriction or endonuclease cleavage of the DNA/RNA complexes, the resulting DNA end can be "polished" if needed for example by removing phosphate groups at the 3' end of the cleaved DNA strand. This can be achieved for example by contacting the cleaved nucleic acids with alkaline phosphatase.

In some embodiments, before ligation, the RNA is disassociated from the first strand cDNA. This can be achieved as desired. In some embodiments, the disassociation comprises heating the complex or treating the complex with an RNAse or otherwise degrading the RNA.

Following cleavage with the restriction enzyme or endonuclease and optional polishing and optional disassociation of RNA from the DNA, an oligonucleotide can be ligated to the 3' end of the first strand cDNA. This can be achieved in a variety of ways depending on whether the restriction enzyme or endonuclease generates a DNA overhang, an RNA overhang, or a blunt end. Ligation will also depend on whether the RNA is dissociated from the first strand cDNA. Several options for ligation format are displayed in FIG. 1.

As shown in option 2 of FIG. 1, in some embodiments, the restriction enzyme or endonuclease leaves a DNA overhang. In these embodiments, a first strand of a double-stranded adaptor oligonucleotide can be annealed to the DNA overhang and the second strand of the double-stranded adaptor oligonucleotide can then be ligated to the 3' end of the cleaved first strand cDNA.

As shown in option 3 of FIG. 1, in some embodiments, the restriction enzyme or endonuclease leaves a DNA/RNA blunt end. In these embodiments, one strand of a blunt-ended double-stranded adaptor oligonucleotide can be ligated to the 3' end of the cleaved first strand cDNA.

As shown in option 4 of FIG. 1, in some embodiments, the restriction enzyme or endonuclease leaves an RNA overhang. In these embodiments, a single-stranded oligonucleotide can be annealed to the RNA overhang and ligated to the 3' end of the cleaved first strand cDNA.

Figure 2:
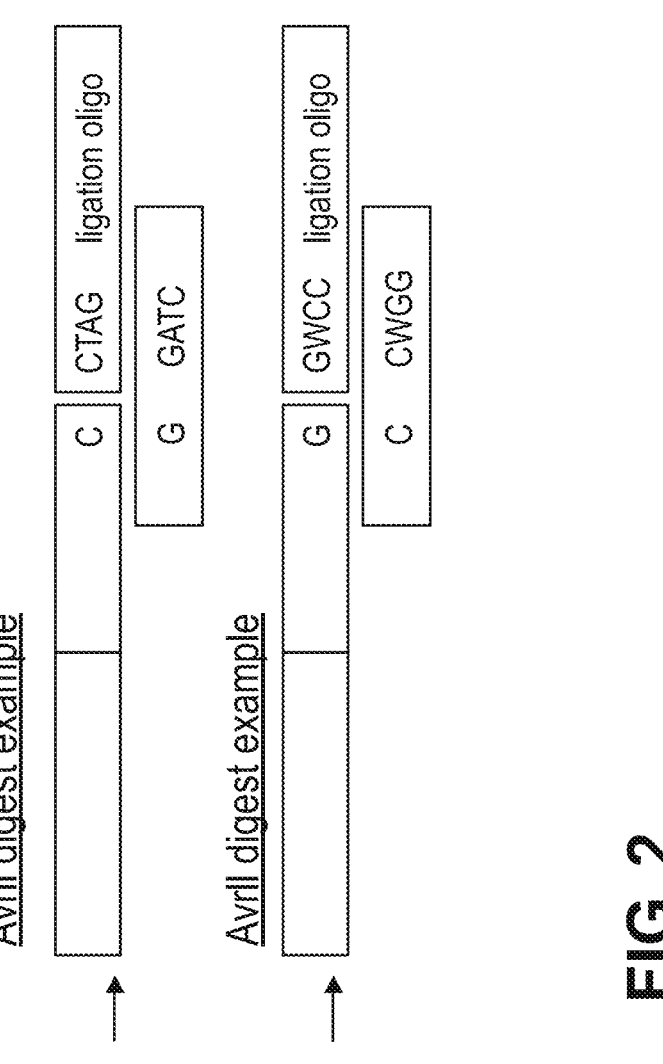
FIG. 2: Ligation Strategies after RNA:DNA heteroduplex cleavage. After cleavage, ligation to the cleaved DNA end can be facilitated by annealing of either a DNA or RNA overhang to either a double stranded DNA or single stranded DNA adaptor. By using the defined restriction enzyme recognition site, oligonucleotides can be specifically ligated to digested cDNA molecules. The digestions from AvrII and AvaII are shown in FIG. 2 as an example to demonstrate non-limiting approaches for ligations. Restriction enzyme digestions using multiple enzymes can lead into ligation approaches using the above approaches with a pool of ligation adaptor specific to the restriction enzymes used.
Figure 3:
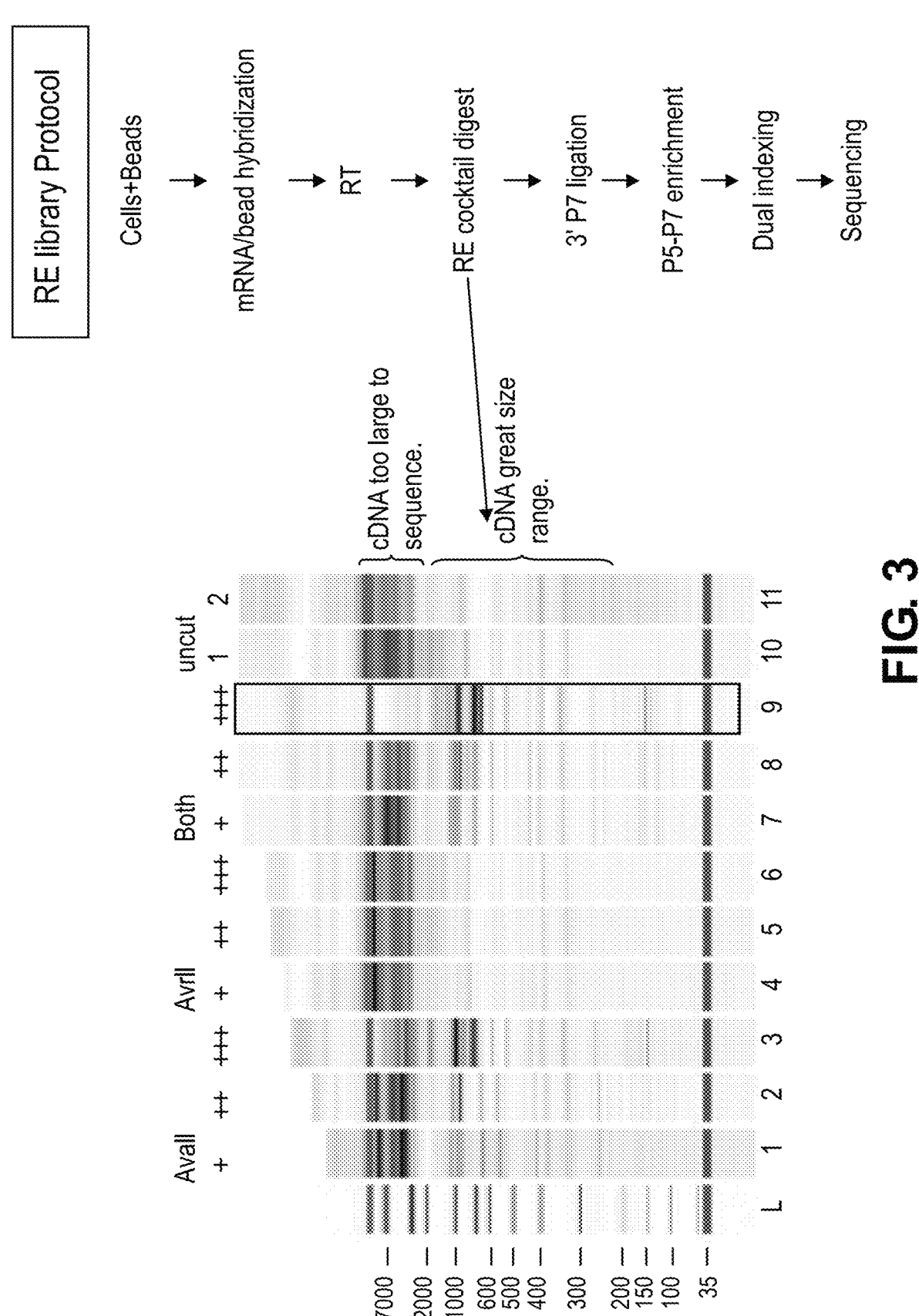
FIG. 3: Restriction enzyme digestion/ligation on TruseqR1 beads' for 3' library generation. One possible workflow is presented on the right of the figure. As shown at the left, the cDNA/RNA complexes can be cleaved with restriction enzymes that cleave DNA/RNA heroduplexes. Advantages of this approach include, for example, that no custom primer is required at the sequencing step, inefficient template-switching oligonucleotide chemistry with possible loss of mRNA diversity is not required, thereby avoiding loss of at least ⅔ sample and possible mRNA diversity at fragmentation and ligation step is avoided.

In any of the above examples, the oligonucleotides can be designed to anneal to the overhangs because the restriction enzyme recognition sequences and cleavage patterns are known and thus the oligonucleotide adaptor sequences can be selected to anneal and be available for ligation. This is depicted, for example in FIG. 2.

In embodiments in which an endonuclease is used instead of a restriction enzyme, the oligonucleotide adaptor options above described for various blunt ends or overhangs can be equally applied for the ends generated by the endonuclease. In some embodiments, the endonuclease cleaves the DNA strand and not the RNA strand of the DNA/RNA duplex, thereby generating an RNA overhang. In these embodiments, in some aspects, a single-stranded oligonucleotide can be annealed to the RNA overhang and ligated to the 3' end of the cleaved first strand cDNA. In these embodiments, in other aspects, the RNA is disassociated from the cDNA strand or otherwise removed or degraded, and a double-stranded oligonucleotide can be annealed to the cDNA 3' end, wherein a first strand of the double-stranded oligo-nucleotide acts as a bridge or splint, annealing to both the 3' end of the cDNA and also the second strand of the double-stranded oligonucleotide (having a 5' phosphate), which in turn can be ligated to the 3' end of the cDNA. Because the endonuclease cleaves in a non-specific manner, the resulting 3' cDNA end will not be predictable (unlike if cleaved by a restriction enzyme) and thus the first strand 3' end can be a random or degenerate (N) sequence (for example but not limited to, at least 4, 5, 6, 7, 8, 9, or 10 contiguous nucleotides) or include one or more non-specific (e.g., "universal") nucleotides (e.g., 2'-deoxyinosine or 5-nitroin-dole) that are capable of base pairing with any of A, C, G, or T.

In any of the embodiments described above, the double-stranded adaptor oligonucleotide can act as a "splint" between the first strand cDNA, to which the double-stranded adaptor oligonucleotide becomes attached, and a second polynucleotide that can be attached (e.g., annealed ligated or both) to the opposite end of the double-stranded adaptor oligonucleotide, thereby adding a further sequence to the 3' end of the first strand cDNA.

The oligonucleotide ligated to the 3' end of the cleaved first strand cDNA can include a PCR handle sequence, or a portion thereof, as well as one or more barcode or other sequences to assist in downstream manipulation or tracking of nucleic acids to which the oligonucleotide is ligated. In some embodiments, a portion of a PCT handle sequence is included on the oligonucleotide and following attachment of the oligonucleotide, a second oligonucleotide having the remaining portion of the PCR handle sequence can be annealed to the product of the first attachment reaction to thereby form the complete PCR handle sequence. See, e.g., WO 2017/117440 describing forming adaptor sequences using two rounds of amplification with different primers to generate a complete adaptor sequence.

As noted herein, the methods described herein can involve generating a first strand cDNA from the RNA, thereby forming a DNA/RNA complex; cleaving the DNA/RNA complex with at least one restriction enzyme or endonuclease that cleaves the DNA/RNA complex and leaves a 3' DNA end and a 5' RNA end; ligating a 5' phosphorylated oligonucleotide to the 3' DNA end to form a first strand cDNA comprising 5'-3': the primer, first strand cDNA and the oligonucleotide; and amplifying the first strand cDNA. In some embodiments, two or more of these steps are performed as a "one-pot" reaction, meaning all of the reagents required for the two or more steps are included in a reaction mixture and the steps discussed above are then performed in sequence without addition of further reagents. In some embodiments, each of the generating, cleaving, ligating and optionally amplifying steps are performed together in a one-pot reaction.

One, two, three or more of the steps described above can also be performed in partitions. In some embodiments, all the generating, cleaving, annealing and ligating are per-formed in a plurality of partitions. In some embodiments, the partitions are droplets or wells. In other embodiments, the partitions can be formed from cells themselves, for example permeabilized and fixed cells. For example in some embodi-ments, the cells are formalin-fixed, paraffin-embedded (FFPE) samples. In fixed permeabilized cells, the reagents can be diffused into the cells for example to cause reverse transcription, cleaving, annealing and/or ligating to occur within the fixed cells. In embodiments that occur in parti-tions of any sort, after the ligating step the contents of the partitions can be combined as the cDNAs will be covalently tagged at that point, allowing for amplification to occur "in bulk."

Once the first strand cDNA having added sequences on the 3' and 5' ends has been formed, the first strand cDNA can be amplified (e.g., using PCR handle sequences as hybrid-ization sites for amplification primers). The amplified cDNA sequences can then be used as desired. In some embodi-ments, the amplified cDNAs can be cloned into a vector or otherwise be formulated into a cDNA library, which can optionally be stored and replicated as desired.

In some embodiments, the amplified cDNAs can be nucleotide sequenced. Any method of nucleotide sequencing can be used as desired so long as at least some of the DNA segments sequence and the barcode sequence is determined. Methods for high throughput sequencing and genotyping are known in the art. For example, such sequencing technolo-gies include, but are not limited to, pyrosequencing, sequencing-by-ligation, single molecule sequencing, sequence-by-synthesis (SBS), massive parallel clonal, mas-sive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety.

Exemplary DNA sequencing techniques include fluores-cence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No. WO 2006/084132, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Addi-tional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511, 803; herein incorporated by reference in their entireties), the 454 picotiter pyrosequencing technology (Margulies et al., 2005 Nature 437, 376-380; U.S. Publication No. 2005/0130173; herein incorporated by reference in their entire-ties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

The practice of the present invention can employ conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999-2010) Current Protocols in Molecular Biology, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag; Sambrook et al., Molecular Cloning: A Laboratory Manual (2nd ed.) (1989).

Example 1

An exemplary protocol for performing methods described herein is provided below:

1. 1 µg of K562 RNA is allowed hybridized with hydrogels beads in 10 µL of GITC lysis buffer at 4 C for 1 hour.
2. Two washes to remove GITC buffer.
3. RT is done using 500 U of Superscript IV in 50 µL reaction volume in presence of USER enzyme to cleave off all oligonucleotides on the hydrogel beads.
4. 0.7× Ampure clean up to remove empty (non-hybridized) oligonucleotides from the cDNA. A bioanalyzer can be used to check the concentration and size distribution.

5. Restriction enzyme digest: 250 U of AvaII is incubated in Buffer Tango with cDNA in 50 µL reaction volume and incubated at 37 C for 3 hours.
6. After 3 hours, spike in 5 U of Shrimp Alkaline Phosphatase and continue incubation at 37 C for additional 30 minutes
7. 2× Ampure to remove AvaII and Alkaline phosphatase. A bioanalyzer can be used to check the concentration and size distribution.
8. Ligation via either Splint Ligase or E coli ligase.
9. 25 U of Splint Ligase is incubated with AvaII digested cDNA/RNA hybrid with 3 pmoles of single stranded p7 DNA adapter # in 20 µL reaction volume in recommended buffer condition. Incubation was done at 25 C and 37 C for 1 hour.
10. For E coli ligase the RE digested cDNA-RNA is denatured at 95 C for 2 minutes before crashing samples on ice for 10 minutes. After which, 10 U of E coli ligase is incubated with AvaII digested cDNA/RNA hybrid with 3 pmoles of double stranded p7 DNA adapter* in 20 µL reaction volume in recommended buffer condition. Incubation is done at 25 C for 1 hour.
11. After ligation, 1.2× ampure is done to remove unused excess adapter. A bioanalyzer can be used to check the concentration and size distribution.
12. Followed by P5-P7 qPCR amplification.
13. After P5-P7 amplification, 0.6× ampure is done to remove primers. A bioanalyzer can be used to check the concentration and size distribution
14. This is followed by dual indexing PCR using Illumina's i5/i7 primers.
15. The libraries are finally cleaned up by using 0.6× ampure. A bioanalyzer can be used to check the concentration and size distribution).

The protocol above was employed with various ligases. Restriction enzymes digested the cDNA/RNA hybrid into smaller fragments and the resulting fragments and their sizes were confirmed with the help of Bioanalyzer trace. Multiple ligases and conditions including splint ligase and E. coli ligase were tested to attach a truncated p7 DNA adaptor at the 3' end of the cDNA fragments. Afterwards, qPCR was performed to amplify the resulting p5-p7 cDNA molecules, the products were confirmed using bioanalyzer and were then indexed using dual indexing. The indexed library size distribution was measured with the help of bioanalyzer and library was quantified using kappa quantification kit. The indexed library was then successfully sequenced.

For the E. coli ligase, a double-stranded adapter sequence was used:

First strand: /5phos/AGATCGGAAGAGCACACGTCT-GAACTCCC (SEQ ID NO: 3);

Second strand: CTCTTCCGATCT S/3 carbon spacer/ (SEQ ID NO: 4);

For the splint ligase, the following single-stranded adapter was used:

```
                                    (SEQ ID NO: 5)
/5phos/GWCAGATCGGAAGAGCACACGTCTGAACTCC.
```

Example 2

Selection of newly synthesized cDNA still annealed to RNA allows for efficient creation of molecular cloning constructs including NGS libraries by selecting for informative cDNAs instead of unused capture oligonucleotides.

Figure 4:
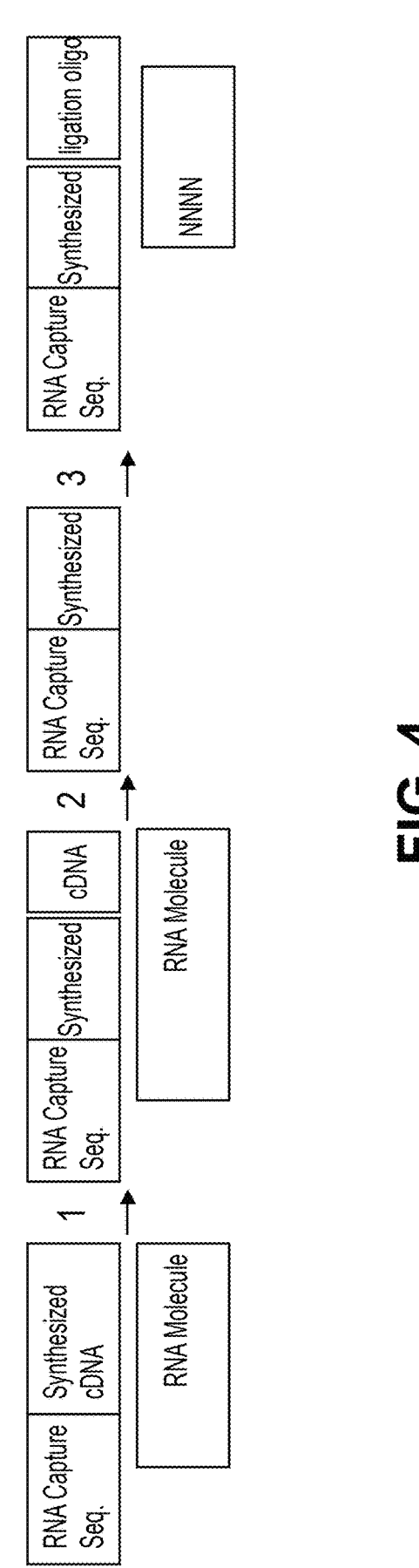
FIG. 4: Ligation Strategies after Duplex Specific Nuclease Cleavage of DNA strand in DNA:RNA heteroduplex. After cleavage (item 1), ligation (item 3) to the cleaved DNA molecule is possible after removal (item 2) of the bound RNA. For example, the uncleaved RNA molecule could be disassociated from the heteroduplex by heat, RNA degrading enzymes, or other approaches to make the cleaved DNA strand accessible. Since the cleavage site is a random sequence, additional efforts must be made to make an efficient ligation. Using a complementary molecule that contains a plurality of sequences in an overlapping extension of the ligation oligonucleotide of interest will allow ligation to the random sequence found on the cleavage site. In addition, universal nucleotides such as but not limited to 2'-deoxyinosine could be used to facilitate efficient ligation to the end of the DNA molecule with a random sequence. Ligation of a known sequence (i.e., at the 5' end of the oligonucleotide ligated to the cDNA) to the 3' end of the cleaved DNA molecule allows down-stream applications such as molecular cloning, NGS library creation, and other molecular techniques.

Cells were lysed in the presence of an oligonucleotide of known sequence as mentioned above (FIG. 4 RNA Capture Oligo) and RNA was annealed to the oligonucleotide. After reverse transcription, the chimeric oligonucleotide containing the cDNA and RNA capture oligo cannot be easily amplified the cDNA sequence 3' end is not known. In addition, full-length cDNA molecules are typically too long for traditional NGS sequencing platforms. Next, the cDNA:RNA heteroduplexes were targeted with a RNA/DNA duplex-specific endonuclease that cleaves the DNA molecule in the cDNA:RNA heteroduplex, but leaves the RNA molecule intact (FIG. 4) After cleavage, the RNA molecule can be dissociated from the cDNA by heat, or RNA degrading enzymes. After release of the cDNA molecule, duplexed oligonucleotides are annealed to the cleaved 3' end of the cleaved cDNA to facilitate ligation of the defined oligonucleotide (FIG. 4). The duplexed oligonucleotides include a first oligonucleotide having 3' overhang of random or universal bases that hybridizes to the cleaved 3' end of the cDNA to facilitate ligation to the phosphorylated 5' end of the second oligonucleotide of the duplex. The second oligonucleotide is ligated to the end of the cleaved cDNA. This is first oligonucleotide of the duplex is a splint or bridge oligonucleotide that improves ligation but is not itself ligated (in other embodiments, a blunt ligation with a single oligonucleotide is an alternative). After ligation, the cleaved cDNA molecule has a known 3' end ligated to it that can be used to PCR amplify, insert the molecule into a cloning vector, and other downstream applications.

The above method was performed as follows: Approximately ten thousand K562 cells were lysed in a buffer containing detergent. An excess of RNA capture oligonucleotide was added to the lysed cells containing (i) a defined sequence for PCR amplification and (ii) an RNA capture sequence of not fewer than 25 nucleotides of thymine with (iii) an additional known sequence to use for downstream PCR amplification. RNA capture oligonucleotides were barcoded and include a unique molecular identifier (UMI) sequence. For this experiment a simplified sequence of the truncated Illumina P5 with a poly T capture sequence was used. (Sequence (Illumina P5 sequence)-CGACGCTCTTCCGATCTTTTTTTTTTTTTTTTTTTTTTT-TTTTTTTT (SEQ ID NO: 6)). To facilitate efficient capture of RNA molecules by the RNA capture oligonucleotide, the RNA capture oligonucleotide was added to the lysed cells at several fold excess of the theoretical amount of RNA molecules per cell, roughly 300,000 RNA molecules per cell, specifically 100-fold excess or 30 million RNA capture oligonucleotides per cell. After lysis, a reaction containing reverse transcriptase was added to the lysate, specifically 500 units of Superscript VI in a total volume of 50 microliters. The RT reaction was then incubated in the temperature optimal for Superscript VI, 50 C, for 1 hour. After incubation, Red Crab Nuclease, referred to here as NUC1, a duplex specific endonuclease, was added to the reaction and incubated for 5 minutes at 50° C. at 0.1, 0.5, or 2 units per reaction. Although the optimal temperature for this enzyme was 65 C, that temperature results in a majority of the RNA:DNA heteroduplex to dissociate thus disrupting the RNA:DNA heteroduplex recognition site and causing a significant decrease in cleavage. Higher than 500 for this enzyme results in less cleavage of product most likely due to the RNA-DNA heteroduplex dissociation, and lower than this (50°) temperature results in less cleavage because the enzyme is not as active at lower temperatures. The 5 minutes could be increased at lower temperatures to give similar results or to increase the size reduction if necessary for a downstream application.

Figure 5:
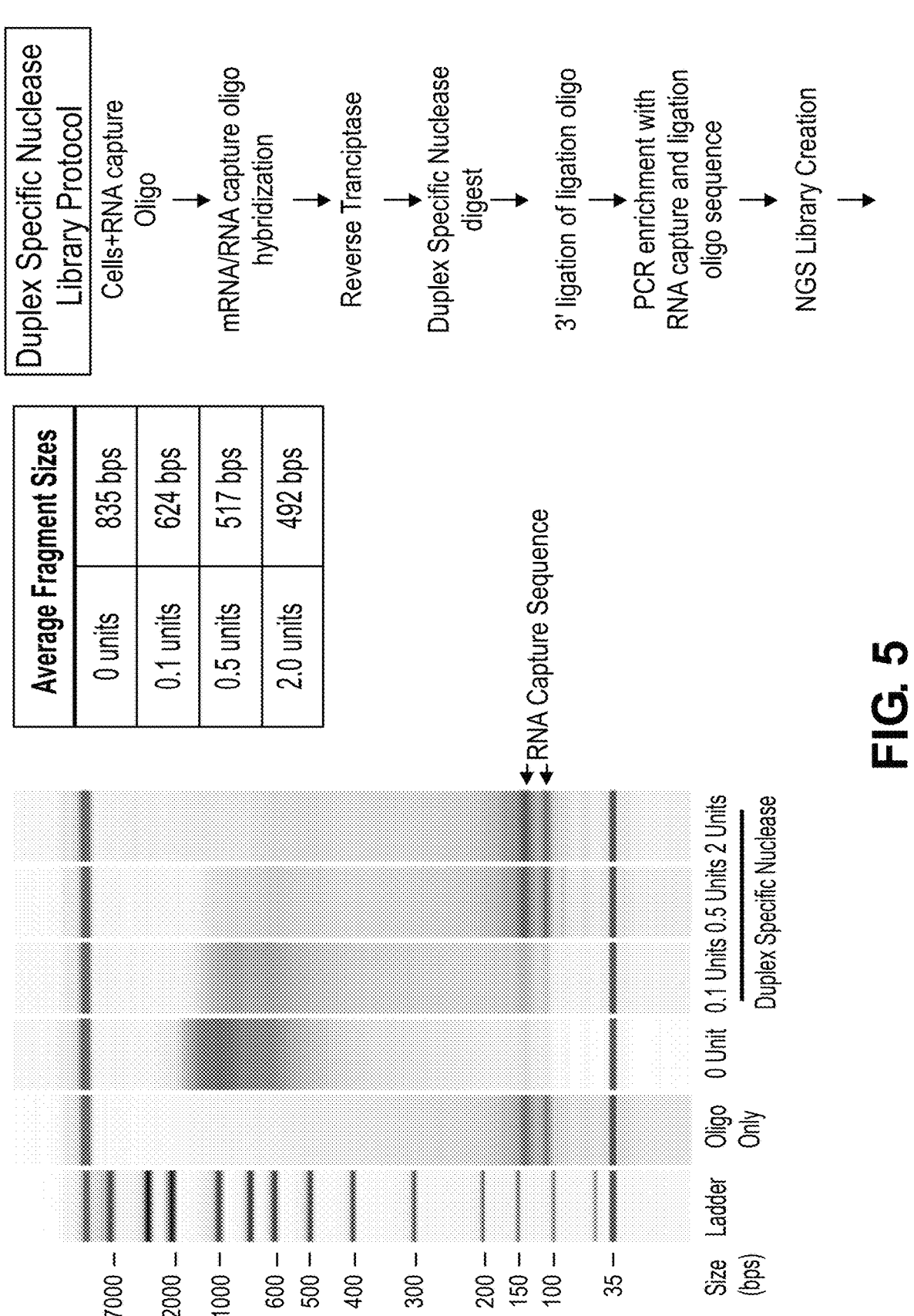
FIG. 5: Duplex Specific Nuclease digestion on cDNA. A schematic of a possible workflow is presented on the right. Cleavage of cDNA amplified from cell lysate using an RNA capture oligo is shown on the left. With increases in duplex specific endonuclease, the reduction of size of cDNA fragments can be observed. The decrease observed was from the average of about 800 base pairs (0 unit), a size too large to successfully sequence by many NGS sequencing platforms, to about 500 base pairs (2 units), a size compatible with those sequencing platforms. Interestingly, the RNA capture oligonucleotide can be observed to be uncleaved even with increasing amounts of duplex specific endonuclease (bands visible around 110 and 140 base pairs) as expected as it is a single stranded DNA molecule. A DNA ladder was run to determine relative size of fragments (ladder).

After duplex-specific endonuclease cleavage, the reaction was heated to 95 C to heat-inactivate enzymes including RT and NUC1 for 2 minutes. Next an excess of ligation oligonucleotide duplex was added to the reaction and ligated using T4 DNA ligase, 200 units per reaction, with adding at least a 3-fold excess of the ligation oligonucleotide duplex. For example, as depicted in FIG. 4, the ligation has two strands: Top strand sequence (Illumina P7 sequence) ACTCTGCGTTGATACCACTGCTT (SEQ ID NO: 7) and bottom strand (splint or bridge oligo) GGTCT-CAACGCAGAGTNNNN (SEQ ID NO: 8). The ligation was then subjected to a PCR amplification using primers complementary to the RNA capture oligonucleotides and ligation oligonucleotide sequence. The Illumina P5 and Illumina P7 sequences were PCR amplified for this step. The PCR amplified product was purified using a SPRI Bead cleanup approach, and a 2 nanogram aliquot was run on an Agilent Bioanalyzer 2000 system and results reported herein (FIG. 5). By tuning the amount of NUC1 endonuclease and the temperature at which it is incubated, the size fragments can be selected for the downstream application and could include a wide range of sizes. In addition, by using defined sequences on either end of the cDNA molecule including but not limited to the sequences required for NGS libraries, this approach can make efficient NGS libraries with customizable library sizes. This approach was very efficient and due to its use of any duplex sequence due to the non-sequence-specific nature of NUC1 cutting, instead of defined restriction enzyme cut sites, yielded more library molecules with the same input as the approach described herein as Example 1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method of generating a cDNA from RNA, the method comprising, generating a first strand cDNA from the RNA by contacting the RNA with one or more primer that anneals to the RNA and extending the primer with a reverse transcriptase, thereby forming a DNA/RNA complex;

cleaving the DNA/RNA complex with a NUC1 endonuclease that cleaves the DNA/RNA complex and leaves a 3' DNA end and a 5' RNA end;

ligating a 5' phosphorylated oligonucleotide to the 3' DNA end to form a first strand cDNA comprising 5'-3': the primer, first strand cDNA and the oligonucleotide; and amplifying the first strand cDNA.

2. The method of claim 1, wherein the RNA is mRNA.

3. The method of claim 1, wherein the ligating comprises annealing a double-stranded oligonucleotide comprising a 5' phosphorylated end to a sequence at the 3' DNA end and contacting the annealed oligonucleotide with a ligase, thereby ligating the 5' phosphorylated end of the oligonucleotide to the 3' DNA end.

4. The method of claim 3, wherein the sequence at the 3' DNA end of the cleaved DNA/RNA complex is a single-stranded overhang.

5. The method of claim 3, wherein after the cleaving and before the ligating the DNA/RNA complex is disassociated.

6. The method of claim 5, wherein the DNA/RNA complex is disassociated by heat.

7. The method of claim 1, wherein the primer comprises (i) a poly dT 3' end that anneals to a 3' poly A sequence on the mRNA or (ii) a gene-specific 3' end that specifically anneals to specific mRNA.

8. The method of claim 1, wherein after the cleaving and before the ligating end repair is performed on the cleaved DNA/RNA complex.

9. The method of claim 8, wherein the end repair comprises contacting the cleaved DNA/RNA complex with alkaline phosphatase.

10. The method of claim 1, wherein the generating, cleaving, annealing and ligating is performed in a plurality of partitions.

11. The method of claim 10, wherein contents of the partitions are combined after the ligating and before the amplifying.

12. The method of claim 1, wherein the primer comprises a barcode and a first PCR handle sequence.

13. The method of claim 10, wherein the primer comprises a partition-specific barcode and a first PCR handle sequence.

14. The method of claim 1, wherein the oligonucleotide comprises 5'-3': a reverse complement of the 5' RNA overhang sequence and a second PCR handle or a fragment thereof or at least three contiguous nucleotides.

* * * * *

SEQUENCE LISTING

Sequence total quantity: 8

```
SEQ ID NO: 1          moltype = DNA  length = 17
FEATURE               Location/Qualifiers
source                1..17
                      mol_type = other DNA
                      organism = synthetic construct
SEQUENCE: 1
cgacgctctt ccgatct                                           17
```

-continued

```
SEQ ID NO: 2            moltype = DNA   length = 18
FEATURE                 Location/Qualifiers
source                  1..18
                        mol_type = other DNA
                        organism = synthetic construct
SEQUENCE: 2
cgtgtgctct tccgatct                                            18

SEQ ID NO: 3            moltype = DNA   length = 29
FEATURE                 Location/Qualifiers
source                  1..29
                        mol_type = other DNA
                        organism = synthetic construct
modified_base           1
                        mod_base = OTHER
                        note = 5'-phosphorylated nucleotide
SEQUENCE: 3
agatcggaag agcacacgtc tgaactccc                                29

SEQ ID NO: 4            moltype = DNA   length = 13
FEATURE                 Location/Qualifiers
source                  1..13
                        mol_type = other DNA
                        organism = synthetic construct
misc_difference         13
                        note = 3' cytidine or guanosine modified with a carbon
                         spacer
SEQUENCE: 4
ctcttccgat cts                                                 13

SEQ ID NO: 5            moltype = DNA   length = 31
FEATURE                 Location/Qualifiers
source                  1..31
                        mol_type = other DNA
                        organism = synthetic construct
modified_base           1
                        mod_base = OTHER
                        note = 5'-phosphorylated nucleotide
SEQUENCE: 5
gwcagatcgg aagagcacac gtctgaactc c                             31

SEQ ID NO: 6            moltype = DNA   length = 44
FEATURE                 Location/Qualifiers
source                  1..44
                        mol_type = other DNA
                        organism = synthetic construct
SEQUENCE: 6
cgacgctctt ccgatctttt tttttttttt tttttttttt tttt              44

SEQ ID NO: 7            moltype = DNA   length = 23
FEATURE                 Location/Qualifiers
source                  1..23
                        mol_type = other DNA
                        organism = synthetic construct
SEQUENCE: 7
actctgcgtt gataccactg ctt                                      23

SEQ ID NO: 8            moltype = DNA   length = 20
FEATURE                 Location/Qualifiers
source                  1..20
                        mol_type = other DNA
                        organism = synthetic construct
misc_difference         17
                        note = a, c, g, t, unknown or other
misc_difference         18
                        note = a, c, g, t, unknown or other
misc_difference         19
                        note = a, c, g, t, unknown or other
misc_difference         20
                        note = a, c, g, t, unknown or other
SEQUENCE: 8
ggtctcaacg cagagtnnnn                                          20
```